United States Patent [19]

Hider et al.

[11] Patent Number: 4,840,958

[45] Date of Patent: Jun. 20, 1989

[54] NOVEL 3-HYDROXYPYRID-2-ONES AND 3-HYDROXYPRID-4-ONES USEFUL IN TREATING PATIENTS HAVING A TOXIC CONCENTRATION OF IRON

[75] Inventors: Robert C. Hider, Essex; George Kontoghiorghes; Jack Silver, both of London, all of England

[73] Assignee: National Research Development Corporation, London, England

[21] Appl. No.: 933,338

[22] Filed: Nov. 20, 1986

Related U.S. Application Data

[63] Continuation of Ser. No. 478,493, Mar. 24, 1983, abandoned.

[30] Foreign Application Priority Data

Mar. 24, 1982 [GB] United Kingdom ............... 8208608

[51] Int. Cl.$^4$ .................. A61K 31/44; C07D 211/86
[52] U.S. Cl. .................................. 514/348; 546/296
[58] Field of Search ....................... 514/348; 546/296

[56] References Cited

PUBLICATIONS

Wilson et al., Textbook of Organic Medicinal And Pharmaceutical Chemistry, Third Edition, pp. 25–27, Lippincott Pub.(1956).
Chew et al., Chem. Abstracts, vol. 94, No. 11, Abst. No. 76572z, Mar. 16, 1981.
Tosato et al., Chem. Abstracts, vol. 92, No. 17, Abst. 146, 042m, Apr. 28, 1980.
Severin, Chem. Abstracts, vol. 85, No. 19, 143, 377u, Nov. 8, 1976.
Goodman and Gillman's, The Pharmacological Basis of Therapeutics, Sixth Edition, MacMillan Publishing Co., Inc., New York.
Yasue, M., Kawamura, N. and Sakakibara, J., "Synthesis from Maltol Glucoside of N-Substituted-3-glucosyloxy-2-methyl-4-pyridones and N-Substituted-3-hydroxy-2-methyl-4-pyridones", pp. 1222–1225, 1970.
Journal of Bacteriology, "Thujaplicins from *Thuja plicata* as Iron Transport Agents for *Salmonella typhimurium*", Akers, Jugh A., Abrego, Victor A. and Garland, Erich, vol. 141, No. 1, Jan. 1980.
Chemical Abstracts, vol. 94, 1981, p. 704.
Chemical Abstracts, vol. 97, 1982, p. 748.
Journal of Pharmaceutical Sciences, vol. 69, No. 9, Sept. 1980, "Pyridones as Potential Antitumor Agents II: 4-pyridones and Bioisosteres of 3-Acetoxy-2-pyridone", Hwang, Deng R., Proctor, George R. and Driscoll, John.
Howard W. Chambers/John E. Casida, "Protective Activity of 1,3-Disubstituted 2-and 6-Pyridones Against Selected Neurotoxic Agents", Toxicology and Applied Pharmacology 14, (1969), pp. 249–258.
Kimiaki Imafuka/Kumio Takahashi/Hisashi Matsumura, "Substituent Effects on 6-Substituted 3-Hyrdoxy-1-Methyl-4-Phridones", Bulletin on the Chemical Society of Japan, vol. 52(1), (1979), pp. 111–113.
Th. Severin/A. Loidl, "Bildung eines Phyridon-Derivates aus Maltose und Lactose", Z. Lebensm, Unters.-Forsch. 161, (1976), pp. 119–124.
Yakugaku .Zasshi, "Maltol Glucoside 3-glucosyloxy-2-methyl-4-pyridone N-3-hydorxy-2-methyl-4-pyridone", 1970, vol. 90, pp. 1222–1225.
R. J. C. Kleipool/J. P. Wibaut, "The Preparation of Some 3-Hydroxy-4-Phridones Substituted on the Nitrogen Atom", RECUEIL (1950), pp. 1041–1047.
Ronald T. Borchardt, "Catechol O-Methyltransferase.4. In Vitro Inhibition by 3-Hydroxy-4-pyrones, 3-Hydorxy-2-pyridones, and 3-Hydroxy-4-pyridones", Journal of Medicinal Chemistry, (1973), vol. 16, No. 5, pp. 581–583.
A. F. Bickel/J. P. Wibaut, "On the Structure of Leucaenine (Leucaenol) from Leucaena Glauca Bentham", Rec. Trav. Chim. 65:65(1946).
von J. P. Wibaut, "Uber die Struktur des Leucaenols (Leucaenin) aus Leucaena glauca Benth", Helvetica Chimica Acta., vol. XXIX, Fasciculus VII, (1946), pp. 1669–1675.
H. Mohrle/H. Weber, "Zur Kenntnis Der 1-Methyl-3-Hydroxypyridone-(2) Und-(6)", Tetrahedron, vol. 26 (1970), pp. 3779–3785.
A. F. Bickel, "On the Structure of Leucaenine (Leucaenol) from Leucaena Glauca Bentham", J. Chem. Soc. 69:1801 (1947).
Hugh A. Akers/Victor A. Abrego/Erich Garland, "Identification of the Thujaplicins from *Thuja plicata* as Iron Transport Agents for *Salmonella typhimurium*", J. of Bacteriol (1980).
Jacobs, Screening for Iron Chelating Drugs, in Development of Iron Chelators for Clinical Use, Matell et al., Editors, Elsevier, North Holland, 1981, pp. 39–46).
Bartulin et al., Bol. Soc. Chil. Quim., 1982, 27, p. 122.
Kimura et al., Chem. Pharm. Bull., 1980, 28, p. 2570.
Hegarty et al., Australian Journal of Biological Sciences, 1978, 31, p. 115.

*Primary Examiner*—Alan L. Rotman
*Attorney, Agent, or Firm*—Oblon, Fisher, Spivak, McClelland & Maier (List continued on next page.)

[57] ABSTRACT

Pharmaceutical compositions containing a 3-hydroxyprid-2-one or 3-hydroxypyrid-4-one in which the hydrogen atom attached to the nitrogen atom is replaced by an aliphatic hydrocarbon group of 1 to 6 carbon atoms and, optionally, in which one or more of the hydrogen atoms attached to ring carbon atoms are replaced by an aliphatic hydrocarbon group of 1 to 6 carbon atoms, or a salt thereof containing a physiologically acceptable cation, are of value for removing toxic amounts of metals, particularly iron, from the body. These compositions are useful in the treatment of iron overloads.

17 Claims, No Drawings

OTHER PUBLICATIONS

Williams, Canadian Journal of Chemistry, 1976, p. 3377.
Pitt and Gupta, Development of Iron Chelators for Clinical Use, Anderson and Hiller (Editors), 1975, p. 137.
Ward and Harris, Australian Journal of Biological Sciences, 1976, 29, p. 189.
Tamhina and Herak, Croatica Chemica Acta CCACAA, 1973, 45, p. 603.
Yakugaku Zasshi, 1970, 90, p. 1222.
Akers, HA et al., J. Bacteriol. 141 (1), 164–168, (1980).
Deng Ruey Hwang & John S. Driscoll, Journal of Pharmaceutical Sciences, vol. 68, No. 7, Jul. 1979.
Deng Ruey Hwang, George R. Proctor & John S. Driscoll;, Journal of Pharmaceutical Sciences, vol. 69, No. 9, Sep. 1980.
Bartulin et al., Chem. Abstracts, No. 97:92048a, p. 748, (1982).
M. Yasue et al., Chemical Abstracts, vol. 74, No. 5, (1971).
R. T. Borchardt et al., Chem. Abstracts, vol. 79, No. 15, (1973).
D. R. Hwang et al., Chemical Abstracts, vol. 94, No. 9, (1982).
H. Moehrle et al., Chem. Abstracts, vol. 73, No. 21, (1970).
"The relationship Between Lipophilicity of Hydroxypyrid-4-One Iron Chelators and Cellular Iron Mobilisation, Using an Hepatocyte Culture Model", by J. B. Porter, M. Gyparaki, E. R. Huehns, R. C. Hider.
"In Vivo Evaluation of Hydroxypyrid-4-One Chelators Intended for the Treatment of Iron Overload by the Oral Route", by M. Gyparaki, J. B. Porter, E. R. Huehns and R. C. Hider.

NOVEL 3-HYDROXYPYRID-2-ONES AND 3-HYDROXYPRID-4-ONES USEFUL IN TREATING PATIENTS HAVING A TOXIC CONCENTRATION OF IRON

This application is a continuation of Ser. No. 478,493, filed Mar. 24, 1983, now abandoned.

BACKGROUND OF THE INVENTION

1. Field of the Invention

This invention relates to compounds for use in pharmaceutical compositions. These compounds are useful for the treatment of iron overloads.

2. Description of the Prior Art

Certain pathological conditions such as thalassaemia, sickle cell anaemia, idiopathic haemochromatosis and aplastic anaemia are treated by regular blood transfusions. It is commonly found that such transfusions lead to a widespread iron overload, which condition can also arise through increased iron absorption by the body in certain other circumstances. Iron overload is most undesirable since, following saturation of the ferritin and transferrin in the body, deposition of iron can occur and many tissues can be adversely affected, particular toxic effects being degenerative changes in the myocardium, liver and endocrine organs. Such iron overload is most often treated by the use of desferrioxamine. However, this compound is an expensive natural product obtained by the culture of Streptomyces and, as it is susceptible to acid hydrolysis, it cannot be given orally to the patient and has to be given by a parenteral route. Since relatively large amounts of desferrioxamine may be required daily over an extended period, these disadvantages are particularly relevant and an extensive amount of research has been directed towards the development of alternative drugs. However, work has been concentrated on three major classes of iron chelating agents or siderophores, namely hydroxamates, ethylenediamine tetra-acetic acid (EDTA) analogues and catechols. The hydroxamates generally suffer from the same defects as desferrioxamine, being expensive and acid labile, whilst the other two classes are ineffective at removing iron from intracellular sites. Moreover, some cathechol derivatives are retained by the liver and spleen and EDTA analogues possess a high affinity for calcium and so are also likely to have associated toxicity problems.

SUMMARY OF THE INVENTION

According to the present invention a pharmaceutical composition comprises a 3-hydroxypyrid-2-one or 3-hydroxypyrid-4-one in which the hydrogen atom attached to the nitrogen atom is replaced by an aliphatic hydrocarbon group of 1 to 6 carbon atoms and, optionally, in which one or more of the hydrogen atoms attached to ring carbon atoms are also replaced by an aliphatic hydrocarbon group of 1 to 6 carbon atoms, or a salt thereof with a physiologically acceptable cation, together with a physiologically acceptable diluent or carrier. Having now briefly described the invention, a more complete understanding of the invention can be obtained by reference to the description of the preferred embodiments which is provided herein for purposes of illustration only, and are not intended to be limiting unless otherwise specified.

DESCRIPTION OF THE PREFERRED EMBODIMENTS

The 3-hydroxypyrid-2- and -4-ones may carry more than one type of aliphatic hydrocarbon group and, in particular, the group attached to the nitrogen atom may be different from any aliphatic hydrocarbon group or groups attached to ring carbon atoms. Groups attached to carbon atoms are, however, more often the same when more than one is present. The aliphatic hydrocarbon groups, whether attached to a nitrogen or a carbon atom, may be cyclic or acyclic, having a branched chain or especially a straight chain in the latter case, and may be unsaturated or especially saturated. Groups of from 1 to 4 carbon atoms and particularly of 1 to 3 carbon atoms are of most interest. Alkyl groups are preferred, for example cyclic groups such a cyclopropyl and especially cyclohexyl but, more particularly preferred are acyclic alkyl groups such as methyl, ethyl, n-propyl and isopropyl. Where the ring carbon atoms are substituted by an aliphatic hydrocarbon group or groups these groups are preferably methyl but in the case of the group substituting the nitrogen atom larger groups may more often be utilised with particular advantage. Substitution of the ring carbon atoms, which is preferably by one rather than two or three aliphatic hydrocarbon groups, is of particular interest in the case of the 3-hydroxypyrid-4-ones, for example at the 6- or particularly the 2-position, whilst the 3-hydroxypyrid-2-ones may more often be used without any additional aliphatic hydrocarbon group substitutent on the ring carbon atoms. Particularly if the ring carbon atoms are substituted by the larger aliphatic hydrocarbon groups, however, there may be an advantage in avoiding substitution on a carbon atom alpha to the

system. This system is involved in the complexing with iron and the close proximity of one of the larger aliphatic hydrocarbon groups may lead to steric effects which inhibit complex formation.

The compound may, if desired, be used in the form of salts thereof containing a physiologically acceptable cation, for example the cation of an alkali metal such as sodium, quaternary ammonium ions or protonated amines such as the cation derived from tris (tris represents 2-amino-2-hydroxymethyl propane 1,3-diol). Salt formation may be advantageous in increasing the water solubility of a compound but, in general, the use of the compounds themselves, rather than the salts, is preferred.

Examples of specific compounds which may be used in compositions according to the present invention are shown by the following formulae (I), (II) and (III):

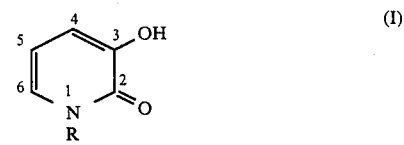

-continued

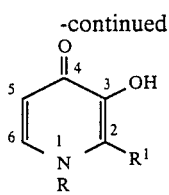
(II)

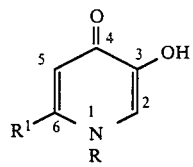
(III)

in which R is an alkyl group, for example methyl, ethyl, n-propyl or isopropyl, and $R^1$ is hydrogen or an alkyl group, for example methyl. Among these compounds and others of use in compositions according to the present invention, the 3-hydroxypyrid-4-ones are of particular interest.

Many of the compounds described above are novel, although some of the compounds of lower molecular weight are known, for example the compound of formula (I) in which R is methyl, the compounds of formula (II) in which R is methyl and $R^1$ is hydrogen or methyl or R is ethyl and $R^1$ is hydrogen, and the compound of formula (III) in which both R and $R^1$ are methyl.

The present invention thus also includes as compounds, per se, a 3-hydroxypyrid-2-one or 3-hydroxypyrid-4-one in which the hydrogen atom attached to the nitrogen atom is replaced by an aliphatic hydrocarbon group and, optionally, in which one or more of the hydrogen atoms attached to ring carbon atoms is also replaced by an aliphatic hydrocarbon group, and salts thereof containing a physiologically acceptable cation, but excluding the specific compounds 3-hydroxy-1-methyl-pyrid-2-one, 3-hydroxy-1-methylpyrid-4-one, 1-ethyl-3-hydroxypyrid-4-one, 3-hydroxy-1,2-dimethylpyrid-4-one and 3-hydroxy-1,6-dimethylpyrid-4-one.

The 3-hydroxy-pyrid-2-one compounds may conveniently be prepared by nucleophilic substitution at the nitrogen atom of the corresponding 2,3-dihydroxypyridine, for example using an organic halide RX in which R represents the aliphatic hydrocarbon group present on the nitrogen atom of the desired 3-hydroxypyrid-2-one and X represents an iodo group. The 3-hydroxypyrid-4-one compounds may conveniently be prepared similarly or preferably from the more readily accessible corresponding 3-hydroxy-4-pyrone. Thus, the 3-hydroxy-4-pyrone may be conveniently be converted to the 3-hydroxypyrid-4-one through protection of the hydroxy group, for example as an ether group such as a benzyloxy group, reaction of the protected compound with a compound $RNH_2$, in which R represents the aliphatic hydrocarbon group present on the nitrogen atom of the desired 3-hydroxypyrid-4-one, in the presence of a base, for example an alkali metal hydroxide such a sodium hydroxide. The protecting group may then be removed. The compounds may be converted to salts formed at the hydroxy group thereof through its conversion to the anion ($OH \rightarrow O^-$) by reaction with the appropriate base according to standard procedures.

It will be appreciated that these are not only routes available to these compounds and that various alternatives may be used as will be apparent to those skilled in the art. In general, however, it is preferred that the compounds are isolated in substantially pure form, i.e. substantially free from by-products of manufacture.

The compounds may be formulated for use as pharmaceuticals for veterinary or particularly human use by a variety of methods. For instance, they may be applied as an aqueous, oily or emulsified composition incorporating a liquid diluent which most usually will be employed for parenteral administration and therefore will be sterile and pyrogen free. However, it will be appreciated from the foregoing discussion in relation to desferrioxamine that oral administration is to be preferred and the compounds of the present invention may be given by such a route. Although compositions incorporating a liquid diluent may be used for oral administration, it is preferred to use compositions incorporating a solid carrier, for example a conventional solid carrier material such as starch, lactose, dectrin or magnesium stearate.

Other forms of administration than by injection or through the oral route may also be considered in both human and veterinary contexts, for example the use of suppositories for human administration.

Compositions may be formulated in unit dosage form, i.e. in the form of discrete portions each comprising a unit dose, or a multiple or sub-multiple of a unit dose. Whilst the dosage of active compound given will depend on various factors, including the particular compound which is employed in the composition, it may be stated by way of guidance that satisfactory control of the amount of iron present in the human body will often be achieved using a daily dosage of about 0.1 g to 5 g, particularly of about 0.5 g to 2 g, veterinary doses being on a similar g/Kg body weight ratio. However, it will be appreciated that it may be appropriate under certain circumstances to give daily dosages either below or above these levels. Where desired, more than one compound according to the present invention may be administered in the pharmaceutical composition or, indeed, other active compounds may be included in the composition.

Although 3-hydroxy-1-methylpyrid-4-one has previously been recognised as a siderophore, it has never before been appreciated that compounds such as this might be used in a pharmaceutical context, and with real advantage. We have found that the 3-hydroxypyrid-2- and -4-ones described above are particularly suited to the removal of iron from patients having an iron overload. The compounds form neutral 3:1 iron complexes at most physiological pH values, and have the advantage that they do not co-ordinate calcium or magnesium. Both the compounds and their complexes will partition into n-octanol indicating that they will permeate biological membranes, this property being confirmed in practice by tests of the ability of the $^{59}Fe$ labelled iron complexes to permeate erythrocytes. The measured coefficients ($K_{part}$) for partition of various of the compounds and their iron complexes are presented in Table 1 of Example 5 hereinafter. Although the ability of both the free compound and its iron complex to permeate membranes is important, it is also desirable for both to possess some degree of water solubility. Preferred compounds show a value of $K_{part}$ for the free compound of above 0.05 but less than 3.0, especially of above 0.2 but less than 1.0, together with a value of $K_{part}$ for the iron complex of above 0.02 but less than 6.0, especially of above 0.2 but less than 1.0. Reference to Table 1 will show that the preferences as to the structure of the compounds in compositions according to the present invention which are expressed hereinbefore lead to compounds which have $K_{part}$ values both in the free state and as iron complexes which are broadly in line with the ranges indicated above.

Both the 3-hydroxypyrid-2-ones and the 3-hydroxypyrid-4-ones possess a high affinity for iron (III), as evidenced by log $K_{sol}$ values {log $K_{sol}$ is defined as being equal to log $\beta_{Fe(L)n} + 21 - [pK_{sp} + n \log a_{L(H+)} + m \log a_L(Ca++)]$ where log $\beta_{Fe(L)n}$ is the cumulative affinity constant of the ligand in question for iron (III), $pK_{sp}$ is the negative logarithm of the solubility product for $Fe(OH)_3$ and has a value of 39, n and m are the number of hydrogen and calcium ions, respectively, which are bound to the ligand, and $a_{L(H+)}$ and $a_L(Ca++)$ are the affinities of the ligand for hydrogen ions and calcium ions, respectively}. In order to solubilise iron (III) hydroxide, log $K_{sol}$ must be greater than 0 and in order to remove iron from transferrin, log $K_{sol}$ should be in excess of 6.0. The log $K_{sol}$ values for 3-hydroxy-1-methylpyrid-2-one and 1,2-dimethyl-3-hydroxypyrid-4-one, by way of example, are 10.0 and 9.5, respectively, thus comparing favourably with those of the bidentate hydroxamates at about 4.0, of catechols at about 8.0, of desferrioxamine at 6.0, and of diethylenetriamine pentaacetic acid (DTPA) at 2.0. Moreover, the ability of the compounds to remove iron efficiently has been confirmed both by in vitro tests and also by in vivo tests in mice. It is particularly significant that these latter tests are successful whether the compound is given intraperitoneally or orally by stomach tube, the compounds being stable under acidic conditions. Oral activity is not generally present among the other types of compound previously suggested for use as iron co-ordinating drugs and although certain EDTA analogues do show such activity, they possess drawbacks for pharmaceutical use.

Although the major use of the compounds is in the removal or iron, they are also of potential interest for the removal of some other metals present in the body in deleterious amounts. The present invention thus includes the use of a 3-hydroxypyrid-2- or -4-one or salt thereof as described above for the removal from the body of toxic amounts of metals, particularly iron. Moreover, the invention also includes a method for the treatment of a patient having toxic amounts of a metal, particularly iron, in the body which comprises administering to said patient an amount of a 3-hydroxypyrid-2- or -4-one or salt thereof as described above to effect a reduction of the levels of this metal in the patient's body.

Having generally described the invention, a more complete understanding can be obtained by reference to the Examples which are provided herein for purposes of illustration only, and are not intended to be limited unless otherwise specified.

EXAMPLES

Example 1

The preparation of 3-hydroxy-1-methylpyrid-2-one 2,3-dihydroxypyridine (5.55 g) is suspended in methyl iodide (20 ml) in a sealed tube and heated for 24 hours at 140° C. The reaction is taken to be complete when a dark brown residue forms as a separate phase from the methyl iodide and the tube is then cooled in solid carbon dioxide and opened. The excess methyl iodide is poured off, distilled water (10 ml) is added to the brown residue, and sulphur dioxide gas is bubbled through the mixture until the aqueous phase becomes clear. The pH of the reaction mixture is adjusted to a value of 6 with 1M aqueous sodium carbonate and the resulting solution then saturated with ammonium sulphate and extracted with chloroform until the chloroform layer no longer gives a blue colouration when added to ferric chloride solution. The chloroform extracts are combined and dried over sodium sulphate. The solvent is then evaporated under vacuum and the resulting residue is crystallized from petroleum ether (b.p. 100°–120° C.) using activated charcoal to give 3-hydroxy-1-methylpyrid-2-one, m.p. 129°–131° C.; $\nu_{max}$ (nujol) 1660, 3100 cm$^{-1}$; $\delta$(d$_6$DMSO) 3.6(s, 3H), 6.1(t, 1H), 6.8(m, 2H), 7.3(s, 1H); M+ 125.

Example 2

The preparation of other 3-hydroxypyrid-2-ones 2,3-dihydroxypyridine is reacted with ethyl iodide, n-propyl iodide and isopropyl iodide under similar conditions to those described in Example 1 for methyl iodide. The reaction mixtures are worked up as described in Example 1 to give the following compounds:

1-Ethyl-3-hydroxypyrid-2-one: m.p. 130°–132° C.; $\nu_{max}$ (nujol) 1620, 3100 cm$^{-1}$; $\delta$(d$_6$DMSO) 1.2(t, 3H), 3.8(m, 2H), 6.0(t, 2H), 6.8(m, 2H), 8.9(s, 1H); M+ 139.

3-Hydroxy-1-propylpyrid-2-one: m.p. 148° C.; $\nu_{max}$ (nujol) 1620, 3150 cm$^{-1}$; $\delta$(d$_6$DMSO) 0.7(t, 3H), 1.5(m, 2H), 3.7(t, 2H), 5.8(t, 1H) 6.5–7.0(m, 2H), 8.7(s, 1H); M+ 153.

3-Hydroxy-1-(2'-methylethyl)pyrid-2-one: m.p. 190° C.; $\nu_{max}$ (nujol) 1660, 3200 cm$^{-1}$; $\delta$(d$_6$DMSO) 1.0(d, 6H), 6.0(m, 1H), 6.5(t, 1H), 6.7(m, 2H); M+ 153.

Example 3

The preparation of 3-hydroxy-1,2-dimethylpyrid-4-one

3-Benzyloxy-2-methyl-4-pyrone

3-Hydroxy-2-methyl-4-pyrone (22.2 g) in methanol 225 ml) is added to aqueous sodium hydroxide (25 ml containing 7.5 g NaOH). Benzyl chloride (25.5 g) is added and the mixture is refluxed for 6 hours and is then allowed to cool overnight. The bulk of the methanol is removed under vacuum and the residue is treated with water (50 ml). The mixture is extracted into dichloromethane (3×25 ml). The extracts are combined, washed with 5% w/v NaOH (2×25 ml), then water (2×25 ml) and dried over magnesium sulphate. Evaporation of the solvent gives crude 3-benzyloxy-2-methyl-4-pyrone (35 g, 92%) which is purified by distillation in nitrogen under reduced pressure to yield a colourless oil (28 g) of b.p. 148° C./0.2 mm.

1,2-Dimethyl-3-benzyloxypyrid-4-one

3-Benzyloxy-2-methyl-4-pyrone (4.8 g) and methylamine hydrochloride (1.56 g) are dissolved in water (200 ml) and ethanol (100 ml) containing sodium hydroxide (2 g) is added. The mixture is stirred at room temperature for 6 days and is then acidified with concentrated hydrochloric acid to pH 2, and evaporated to dryness. The resulting colourless solid is washed with water and extracted into chloroform (2×50 ml). The chloroform extracts are combined, dried over magnesium sulphate, and evaporated to yield 1,2-dimethyl-3-benzyloxypyrid-4-one (3.2 g).

1,2-Dimethyl-3-hydroxypyrid-4-one 1,2-Dimethyl-3-benzyloxypyrid-4-one (2 g) is added to concentrated hydrobromic acid (10 ml) and heated in a steam bath for 30 minutes. The resulting mixture is then recrystallised from water to yield 1,2-dimethyl-3-hydroxypyrid-4-one (1 g), m.p. 230° C. (with decomposition); $\nu_{max}$ (nujol) 1620, 3150 cm$^{-1}$; $\delta$(d$_6$DMSO) 2.3(s, 3H), 3.8(s, 3H), 6.9(d, 1H), 7.8(d, 1H); M+ 139.

Example 4

The preparation of other 3-hydroxypyrid-4-ones

3-Benzyloxy-2-methyl-4-pyrone is prepared as described in Example 3 and is reacted with ethylamine, n-propylamine, isopropylamine, n-butylamine and n-hexylamine hydrochloride under similar conditions to those described in Example 3 for methylamine hydrochloride. The reaction mixture is worked up and the hydroxy group deprotected as described in Example 3 to give the following compounds:

1-Ethyl-3-hydroxy-2-methylpyrid-4-one: m.p. 190°–195° C.; $\nu_{max}$ (nujol) 1620, 3150 cm$^{-1}$; $\delta$(d$_6$DMSO) 1.1(t, 3H), 2.6(s, 3H), 3.5(m, 2H), 7.3(d, 1H), 8.5(d. 1H); M+ 153.

3-Hydroxy-2-methyl-1-propylpyrid-4-one: m.p. 182°–183° C.; $\nu_{max}$ (nujol) 1630, 3200 cm$^{-1}$; $\delta$(d$_6$DMSO) 0.9(t, 3H), 1.6(m, 2H), 2.43(s, 3H), 4.2(t, 2H), 7.1(d, 1H), 8.15(d, 1H); M+ 167.

3-Hydroxy-2-methyl-1-(1'-methylethyl)pyrid-4-one: m.p. 198°–200° C.; $\nu_{max}$ (nujol) 1630, 3150 cm$^{-1}$; $\delta$(d$_6$DMSO) 1.28(d, 6H), 2.43(s, 3H), 4.8(m, 1H), 7.15(d, 1H), 8.15(d, 1H); M+ 167.

1-Butyl-3-hydroxy-2-methylpyrid-4-one: m.p. 188°–190° C.; $\nu_{max}$ (nujol) 1630, 3200 cm$^{-1}$; $\delta$(d$_6$DMSO) 0.9(t, 3H), 1.3(m, 4H), 2.41(s, 3H), 4.2(t, 2H), 7.2(d, 1H), 8.3(d, 1H); M+ 181.

1-Hexyl-3-hydroxy-2-methylpyrid-4-one: m.p. 166°–168° C.; $\nu_{max}$ (nujol) 1630, 3200 cm$^{-1}$; $\delta$(d$_6$DMSO) 0.8(t, 3H), 1.3(m, 8H), 2.5(s, 3H), 4.2(t, 2H), 7.4(d, 1H), 8.3(d, 1H); M+ 209.

Example 5

Partition data on 3-hydroxypyrid-2- and -4-ones and their iron complexes

The partition coefficient $K_{part}$, being the ratio (concentration of compound in n-octanol)/(concentration of compound in aqueous phase) on partition between n-octanol and aqueous tris hydrochloride (20 mM, pH 7.4), is measured at 20° C. for various of the compounds of Examples 1 to 4 and for their iron complexes (at 10$^{-4}$M) by spectrophotometry. Acid washed glassware is used throughout and, following mixing of 5 ml of the 10$^{-4}$M aqueous solution with 5 ml n-octanol for 1 minute, the aqueous n-octanol mixture is centrifuged at 1,000 g for 30 seconds. The two resulting phases are separated for a concentration determination by spectrophotometry on each. For the free hydroxypyridones, the range 220–340 nm is used for concentration determination whilst for the iron complexes, the range 340–640 nm is used.

Values typical of those obtained are shown in Table 1 where it will be seen that quite small changes in structure such as the replacement of a 1-propyl group by a 1-(1'-methylethyl) group can produce quite large differences in $K_{part}$ values.

TABLE 1

| | Partition coefficients | |
|---|---|---|
| | Partition Coefficient, $K_{part}$ | |
| Compound | Free Compound | Iron complex [Fe$^{III}$—(compound)$_3$] |
| 3-hydroxy-1-methylpyrid-2-one | 0.44 | 0.10 |
| 1-ethyl-3-hydroxypyrid-2-one | 0.52 | 1.06 |
| 3-hydroxy-1-propylpyrid-2-one | 0.78 | 6.20 |
| 3-hydroxy-1-(1'-methylethyl)-pyrid-2-one | 3.10 | 13.50 |
| 3-hydroxy-1,2-dimethylpyrid-4-one | 0.21 | 0.05 |
| 1-ethyl-3-hydroxy-2-methylpyrid-4-one | 0.40 | 0.03 |
| 3-hydroxy-2-methyl-1-propylpyrid-4-one | 0.67 | 0.53 |
| 3-hydroxy-1-(1'-methylethyl)-2-methylpyrid-4-one | 0.95 | 0.20 |
| 1-butyl-3-hydroxy-2-methylpyrid-4-one | 5.30 | 7.70 |

Example 6

In vitro tests of an iron binding capacity

The 3-hydroxypyridones used in this Example were prepared as described in Examples 1 to 4.

(1) Mobilisation of iron from ferritin

Horse spleen ferritin (Sigma) was used without further purification and its iron content was estimated spectrophotometrically at 420 nm. The ferritin solution in phosphate buffered saline (Dulbecco-OXOID, 10$^{-6}$M, pH 7.4) was enclosed in a Visking dialysis tube and dialysed against a 3×10$^{-3}$M buffered solution of one of various pyridones as indicated in Table 2. The absorption spectrum of the resulting iron (III) complex in the dialysis solution was recorded after 6 and 24 hours. For comparative purposes, the procedure was repeated using a blank control.

The results are shown in Table 2 where the percentage of ferritin-bound iron removed by the compound under test is shown. For comparative purposes, results reported in the literature for similar tests with 1×10$^{-3}$M desferrioxamine (Crichton et al, J. Inorganic Biochem., 1980, 13, 305) and with 6×10$^{-3}$M LICAMS (Tufano et al, Biochem. Biophys. Acta, 1981, 668, 420) are also given in the Table. It will be seen that the pyridone compounds are able to remove iron effectively from ferritin in contrast with desferrioxamine and LICAMS (although the latter will remove iron in the presence of ascorbic acid such a mixture is very difficult to manage clinically). These results shown in Table 2 have been confirmed by separating apoferritin and the 3-hydroxypyridone iron complex from the reaction product in each case by chromatography on Sephadex G10.

TABLE 2

| Removal of iron from ferritin | | |
|---|---|---|
| | Percentage of iron removed | |
| Compound | 6 hours | 24 hours |
| Control | 0 | 0 |
| 3-hydroxy-1-methylpyrid-2-one | 11 | 22 |
| 1-ethyl-3-hydroxypyrid-2-one | 14 | 24 |
| 3-hydroxy-1-propylpyrid-2-one | 11 | 21 |
| 3-hydroxy-1-(1'-methylethyl)-pyrid-2-one | 11 | 20 |
| 3-hydroxy-1,2-dimethylpyrid-4-one | 14 | 31 |

TABLE 2-continued

| | Removal of iron from ferritin | |
|---|---|---|
| | Percentage of iron removed | |
| Compound | 6 hours | 24 hours |
| 1-ethyl-3-hydroxy-2-methylpyrid-4-one | 19 | 34 |
| 3-hydroxy-2-methyl-1-propylpyrid-4-one | 15 | 26 |
| 3-hydroxy-2-methyl-1-(1'-methylethyl)-pyrid-4-one | 17 | 24 |
| 1-butyl-3-hydroxy-2-methylpyrid-4-one | 6 | 7 |
| Desferrioxamine (1 mM) | 1.5 | — |
| LICAMS (6 mM) | 0 | — |
| LICAMS (6 mM + 12 mM ascorbic acid) | 7 | — |

(2) Mobilisation of iron from transferrin

Human transferrin (Sigma) was loaded with iron (III) by the method of Bates and Schlaback, J. Biol. Chem. (1973) 248, 3228. $^{59}$Iron (III) transferrin ($10^{-5}$M) was incubated with a $4 \times 10^{-3}$M solution in tris HCl (0.1M, pH 7.4) of one of various pyridones as indicated in Table 2 for periods of 4 hours and 18 hours. The solution was then dialysed against phosphate buffered saline for 24 hours. The $^{59}$Fe remaining in the dialysis tube was then recorded. For comparative purposes, this procedure was repeated with desforrioxamine using incubation for both 4 hours and 18 hours and with EDTA using incubation for 4 hours only.

The results are shown in Table 3 in terms of the percentage of transferrin bound iron removed by the compound under test. It will be seen that the pyrid-4-one compounds are very effective at iron removal, as compared with desferrioxamine or EDTA, after only 4 hours. Although the efficiency at iron removal of the pyrid-2-one compounds is only at a similar level to that of desferrioxamine and EDTA after 4 hours, it increases markedly after 18 hours whereas the level for desferrioxamine at 18 hours is substantially similar to that at 4 hours.

Similar relative levels of efficiency were observed when the iron was measured spectrophotometrically. Moreover, the results shown in Table 3 have been confirmed by separating apotransferrin and the 3-hydroxypyridone iron complex from the reaction product in each case by chromatography on Sephadex G10.

TABLE 3

| | Percentage of iron removed | |
|---|---|---|
| Compound | 4 hours | 18 hours |
| Control | 0 | 0 |
| 3-hydroxy-1-methylpyrid-2-one | 11 | 62 |
| 1-ethyl-3-hydroxypyrid-2-one | 12 | 52 |
| 3-hydroxy-1-propylpyrid-2-one | 15 | 45 |
| 3-hydroxy-1-(1'-methylethyl)-pyrid-2-one | 17 | 57 |
| 3-hydroxy-1,2-dimethylpyrid-4-one | 90 | 91 |
| 1-ethyl-3-hydroxy-2-methylpyrid-4-one | 88 | 90 |
| 3-hydroxy-2-methyl-1-propylpyrid-4-one | 90 | 92 |
| 3-hydroxy-2-methyl-1-(1'-methylethyl)-pyrid-4-one | 94 | 94 |
| Desferrioxamine | 17 | 22 |
| EDTA | 27 | — |

Example 7

In vivo tests of iron binding capacity

The 3-hydroxypyridones used in this Example were prepared as described in Examples 1, 2 and 3.

Mice were injected intraperitoneally with iron dextran (2 mg) at weekly intervals over a four week period. Two weeks after the final injection, the mice were injected via the tail vein with $^{59}$Fe lactoferrin (human lactoferrin, 1 mg per injection 2Ci). The mice were then caged individually. After a ten day period, one of the various pyridones listed in Table 4 was administered to groups of mice at 10 mg per mouse either intraperitoneally or intragastrically. The excretion of iron was recorded at either 12 or 24 hourly intervals over a three day period before and a two day period after administration of the compound. For comparative purposes, the procedure was repeated with a blank control and with desferrioxamine, also at 10 mg per mouse.

The results are shown in Table 4, being given on the basis of the control representing 100% excretion, and illustrate the particular advantage of the pyridones as compared with desferrioxamine for oral administration. It should be mentioned that the large standard deviation (SD) values are somewhat misleading as uniformly positive results can yield high SDs which might be taken to suggest that the results are not significantly different from zero. However, this is not the case here, the large SD values being a consequence of the large range among the positive responses (the range of values obtained is given in the Table for each compound).

TABLE 4

| | Excretion of iron in vivo | | | |
|---|---|---|---|---|
| | Intraperitoneal Administration | | Intragastric Administration | |
| Compound | Number of Mice | Excretion of $^{59}$Fe ± SD (Range of values) percent | Number of Mice | Excretion of $^{59}$Fe ± SD (Range of values) percent |
| Control | 12 | 100 ± 10 | — | — |
| 3-hydroxy-1-methyl-pyrid-2-one | 7 | 150 ± 30 (107–192) | 3 | 235 ± 30 |
| 1-ethyl-3-hydroxy-pyrid-2-one | 13 | 223 ± 117 (133–590) | 13 | 188 ± 66 (95–303) |
| 3-hydroxy-1-propylpyrid-2-one | 13 | 169 ± 49 (112–280) | 13 | 149 ± 56 (53–260) |
| 3-hydroxy-1,2-dimethylpyrid-4-one | 7 | 265 ± 70 (181–401) | 3 | 320 ± 90 (242–425) |
| Desferrioxamine | 7 | 340 ± 90 (172–472) | 3 | 90 ± 20 (80–107) |

Having now fully described the invention, it will be apparent to one of ordinary skill in the art that many changes and modifications can be made thereto, without departing from the spirit or scope of the invention as set forth herein.

What is claimed as new and desired to be secured by Letters Patent of the United States is:

1. A method for the treatment of a patient having a toxic concentration of iron in the body, comprising:

administering to said patient by mouth, by the bowel or by parenterally an amount effective to reduce said toxic concentration of a 3-hydroxypyrid-2-one or 3-hydroxypyrid-4-one compound, said compounds having the formula:

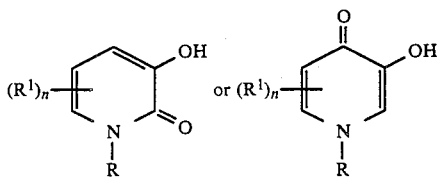

wherein

R is an unsubstituted $C_1$–$C_3$ hydrocarbon group;

$R^1$ is an unsubstituted $C_1$–$C_3$ hydrocarbon group; and n is 0, 1 or 2;

or a physiologically acceptable salt thereof.

2. The method of claim 1, wherein R is an acyclic alkyl group.

3. The method of claim 1, wherein R and $R^1$ are the same or different and are selected from the group consisting of methyl, ethyl, n-propyl and isopropyl.

4. The method of claim 1, wherein the said compound is a 3-hydroxypyrid-4-one.

5. The method of claim 4, wherein n is 1 and $R^1$ is at either the 2- or the 6-position of said 3-hydroxypyrid-4-one.

6. The method of claim 4, wherein n is 1 and $R^1$ is at the 2-position of said 3-hydroxypyrid-4-one.

7. The method of claim 1, wherein said compound is a 3-hydroxypyrid-2-one and n is 0, said pyridone being substituted only at the nitrogen atom.

8. The method of claim 5, wherein R and $R^1$ are the same or different and are selected from the group consisting of methyl, ethyl, n-propyl and isopropyl.

9. The method of claim 8, wherein R is methyl.

10. The method of claim 6, wherein R and $R^1$ are the same or different and are selected from the group consisting of methyl, ethyl, n-propyl and isopropyl.

11. The method of claim 10, wherein $R^1$ is methyl.

12. The method of claim 1, wherein said compound is at least one member selected from the group consisting of 3-hydroxy-1-methylpyrid-2-one, 1-ethyl-3-hydroxypyrid-2-one, 3-hydroxy-1-propylpyrid-2-one, 3-hydroxy-1-(1'-methylethyl)-pyrid-2-one, 3-hydroxy-1,2-dimethylpyrid-4-one, 1-ethyl-3-hydroxy-2-methylpyrid-4-one, 3-hydroxy-2-methyl-1-propylpyrid-4-one, 3-hydroxy-1-(1'-methylethyl)-2-methylpyrid-4-one, and physiologically acceptable salts thereof.

13. The method of claim 1, wherein said compound is 3-hydroxy-1,2-dimethylpyrid-4-one or a physiologically acceptable salt thereof.

14. The method of claim 1, wherein said compound is 1-ethyl-3-hydroxy-2-methylpyrid-4-one or a physiologically acceptable salt thereof.

15. The method of claim 1, wherein said compound is 3-hydroxy-2-methyl-1-propylpyrid-4-one or a physiologically acceptable salt thereof.

16. The method of claim 1, wherein said compound is 3-hydroxy-1-(1'-methylethyl)-2-methylpyrid-4-one or a physiologically acceptable salt thereof.

17. The method of claim 1, wherein said compound is in the free form.

* * * * *

UNITED STATES PATENT AND TRADEMARK OFFICE
CERTIFICATE OF CORRECTION

PATENT NO. : 4,840,958

DATED : JUNE 20, 1989

INVENTOR(S) : HIDER et al

It is certified that error appears in the above-identified patent and that said Letters Patent is hereby corrected as shown below:

Column 11 line 11 delete "by"

Signed and Sealed this

Nineteenth Day of March, 1991

Attest:

HARRY F. MANBECK, JR.

Attesting Officer

Commissioner of Patents and Trademarks